United States Patent [19]

Braye

[11] 4,127,580
[45] Nov. 28, 1978

[54] PROCESS FOR THE PREPARATION OF THIENO-PYRIDINE DERIVATIVES

[75] Inventor: Emile Braye, Auterive, France

[73] Assignee: Parcor, Paris, France

[21] Appl. No.: 775,314

[22] Filed: Mar. 7, 1977

Related U.S. Application Data

[63] Continuation of Ser. No. 652,805, Jan. 27, 1976, abandoned.

[30] Foreign Application Priority Data

Feb. 7, 1975 [FR] France ............................. 75 03968
Jul. 30, 1975 [FR] France ............................. 75 23786

[51] Int. Cl.² .................................................. C07D 283/00
[52] U.S. Cl. ..................................... 546/114; 424/256
[58] Field of Search ................................ 260/294.8 C

[56] References Cited

U.S. PATENT DOCUMENTS

| 4,065,459 | 12/1977 | Heymes et al. ............... 260/294.8 C |
| 4,075,340 | 2/1978 | Maffrand ........................ 260/294.8 C |

Primary Examiner—Alan L. Rotman
Attorney, Agent, or Firm—Young & Thompson

[57] ABSTRACT

This invention relates to a process for the preparation of thieno-pyridine derivatives having the structural formula:

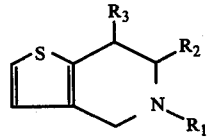

in which $R_1$ represents an optionally substituted alkyl, aryl or aralkyl radical, and $R_2$ and $R_3$ represent each hydrogen or a lower alkyl, aryl or heterocyclic radical, comprising:

(a) reacting a derivative of the formula

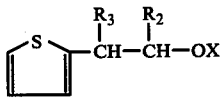

in which $R_2$ and $R_3$ are as defined for formula (I) and X represents hydrogen, or an alkali metal, or a radical Mg-Y in which Y represents halogen, with a halo-sulfonyl derivative having the formula:

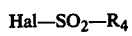

in which Hal represents halogen and $R_4$ represents an optionally substituted alkyl, aryl or aralkyl group, to give a compound having the formula:

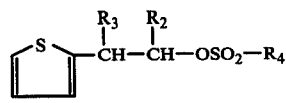

(b) subsequently reacting the latter compound with an amine of the formula:

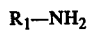

in which $R_1$ is as defined for the formula (I), to give a compound having the formula:

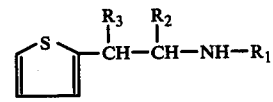

and (c) subsequently cyclizing compound (VI) with formaldehyde to give the derivative of the formula (I).

8 Claims, No Drawings

PROCESS FOR THE PREPARATION OF THIENO-PYRIDINE DERIVATIVES

This is a continuation of application Ser. No. 652,805, filed Jan. 27, 1976, now abandoned.

This invention relates to a new process for the preparation of thieno-pyridine derivatives having the structural formula:

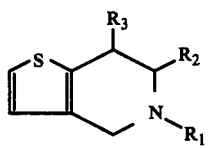
(I)

in which $R_1$ represents an optionally substituted alkyl, aryl or aralkyl radical, and $R_2$ and $R_3$, which may be the same or different, represent each hydrogen or a lower alkyl, aryl or heterocyclic radical.

4,5,6,7-Tetrahydro-thieno[3,2-c]pyridine derivatives of this type have already been described, together with their therapeutic applications, namely, for their anti-inflammatory, vasodilatator and blood plate aggregation inhibitor action, and a process for their preparation in U.S. Pat. No. 4,051,141, Sept. 27, 1977, which was a streamlined division of Ser. No. 435,036, filed Jan. 21, 1974, which in turn corresponded to French application Ser. No. 73 03503 filed Feb. 1, 1973. Said process comprises condensing a compound of the formula:

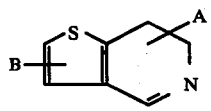

in which A and B represent each at least an atom or group selected from hydrogen, halogen, or a hydroxy, lower alkyl, lower alkoxy, nitro or amino group, with a halide of the formula Hal-R in which Hal represents a halogen atom and R is an optionally substituted alkyl, aryl or aralkyl radical, to give a pyridinium salt having the formula:

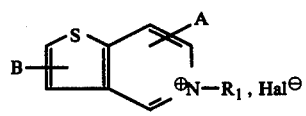

and subsequently hydrogenating the pyridinium salt to give the derivative of the formula (I).

This process, however, is expensive and cumbersome to operate in that it requires numerous difficult operating steps.

The object of the present invention is to overcome such drawbacks and to provide a simple inexpensive process for the preparation of the aforementioned pyridine derivatives.

Thus, the invention relates to a process for the preparation of compounds of the aforementioned formula (I), comprising (a) reacting a derivative of the formula:

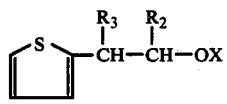
(II)

in which $R_2$ and $R_3$ are as defined for formula (I) and X represents hydrogen, or an alkali metal, or a radical Mg-Y in which Y represents halogen, with a halo-sulfonyl derivative having the formula

(III)

in which Hal represents halogen and $R_4$ represents an optionally substituted alkyl, aryl or aralkyl group, to give a compound having the formula:

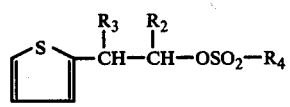
(IV)

(b) subsequently reacting the latter compound with an amine of the formula:

(V)

in which $R_1$ is as defined for the formula (I), to give a compound having the formula:

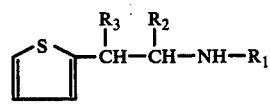
(VI)

and (c) subsequently cyclising compound (VI) with formaldehyde to give the derivative of the formula (I).

The process of this invention may be illustrated by means of the following reaction scheme:

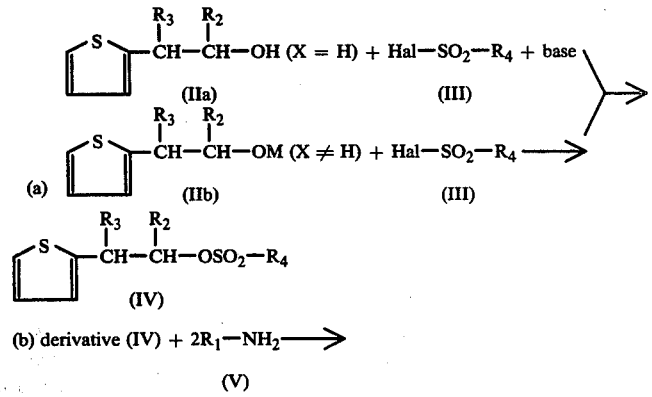

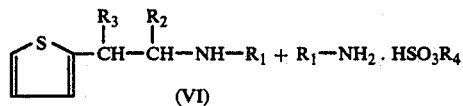

(VI)

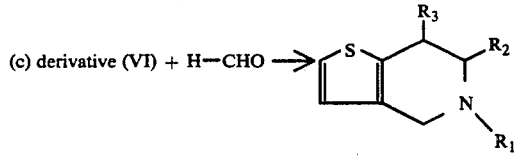

(c) derivative (VI) + H—CHO →

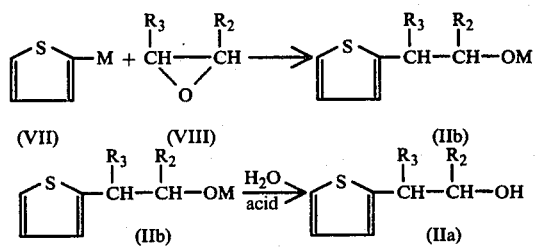

The compounds of the formula (IIa) or (IIb) [2-(2-thienyl)ethanolic derivatives] may be obtained by reacting a thiophene metallation product of the formula (VII) with an oxiran of the formula (VIII), according to the following reaction scheme:

$$\begin{array}{c} \underset{(VII)}{\text{S—M}} + \underset{(VIII)}{\overset{R_3\ R_2}{\underset{O}{CH—CH}}} \longrightarrow \underset{(IIb)}{\overset{R_3\ R_2}{\text{S—CH—CH—OM}}} \\ \underset{(IIb)}{\overset{R_3\ R_2}{\text{S—CH—CH—OM}}} \xrightarrow[\text{acid}]{H_2O} \underset{(IIa)}{\overset{R_3\ R_2}{\text{S—CH—CH—OH}}} \end{array}$$

In the derivatives of the formula (IIb) and (VII), M represents an alkali metal such as lithium, sodium and potassium, or a Mg-Y radical, Y being halogen and $R_2$ and $R_3$ having the afore-defined meanings.

Thiophene metallation may generally be effected with any suitable known reagent for that purpose, such as organolithium derivatives RLi in which R is methyl, ethyl, propyl, isopropyl, butyl, isobutyl, amyl, phenyl, substituted phenyl, etc., preferably methyl lithium, ethyl lithium and n-butyl lithium; organosodium derivatives of the formula RNa in which R has the above defined meaning; or organopotassium derivatives of the formula RK in which R has the above defined meaning. Thiophene metallation may also be effected via a GRIGNARD reaction which leads to the corresponding organomagnesium compound.

The derivative of the formula (IIa) (X = H) may be obtained by hydrolysis of the derivative of the formula (IIb). When derivative (IIa) is used in the reaction of step (a) with the halo-sulfonated derivative Hal—SO$_2$—R$_4$, the reaction is effected in the presence of a base which may be selected from the tertiary amines of trialkylamine or aryldialkylamine type, or from the pyridine or quinoline derivatives, or also from inorganic derivatives of weak acids (e.g., alkali metal carbonates, alkali metal or alkali-earth metal hydrides, metal alkoxides).

Examples of useful halo-sulfonyl derivatives include methane sulfonyl chloride, trichloromethane sulfonyl chloride, trifluoromethane sulfonyl chloride, benzene sulfonyl chloride, para-toluene sulfonyl chloride, m.a-cetyl benzene sulfonyl fluoride or p.bromophenyl sulfonyl chloride.

The animation reaction of step (b) of the process of this invention is advantageously effected using excess amine R$_1$—NH$_2$ which may be readily recovered and recycled for subsequent use.

This reaction is advantageously effected in the hot, within a polar solvent such as acetonitrile, ethanol or pyridine, for example.

According to an embodiment of the invention, the cyclisation reaction of step (c) with formaldehyde is effected in a single step, advantageously in acidic medium within an inert solvent such as water or ethanol or a mixture of both, or within any solvent which is stable in acidic medium. It is advantageous to operate at the boiling temperature of the solvent and with an equimolar mixture of derivative of the formula (VI) and formaldehyde.

According to another embodiment, the desired compounds of the formula (I) may be obtained in improved yields by effecting the cyclisation in two distinct steps, viz.: (a) reaction of formaldehyde with the derivative of the formula (VI) in aqueous medium, and isolation of the water-free product, followed by (b) reaction of the compounds obtained in (a) with a solution of dry hydrochloric acid in an aprotic polar solvent.

Preparation of compounds of the formula (I) according to the above-described procedure makes it possible to attain yields of the order of about 80%, whereas the yields are about 40% via direct cyclisation.

The compounds obtained on completion of step (a) of reaction of formaldehyde with the compound of the formula (VI) have a structure which is not yet fully understood and which, purely for indicative purposes, may be represented by the structures of the following types:

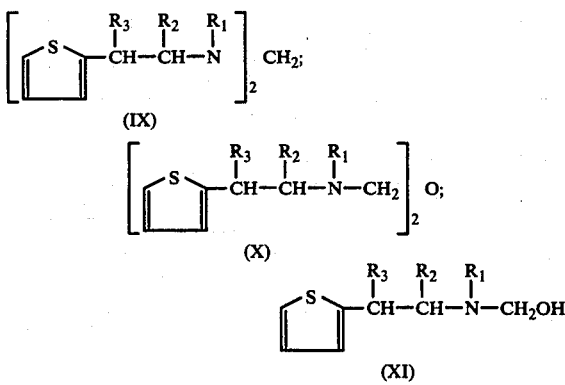

The compound (IX) in which $R_3=R_2=H$ and $R_1=CH_2-\bigcirc\!\!-Cl$ was isolated from the mixture and characterized by elemental analysis and NMR spectroscopic analysis.

It is essential that the addition product or products of formaldehyde and the compound of the formula (VI) be isolated and obtained free from water. However, they may be used in the next step as a solution in an inert solvent such as benzene, toluene or any other similar solvent compatible with the nature of the products, the essential point being that such a solution be anhydrous.

The product or products obtained in step (a) are added to a solution of dry hydrochloric acid in an aprotic polar solvent, preferably dimethyl formamide. Other solvents of similar nature, such as dimethylsulfoxide, N-methylpyrrolidone, N,N-dimethylacetamide, etc. may also be used. It is useful to select the solvent so that the hydrochloride of the compound of the formula (I) will be as sparingly soluble therein as possible, in order to facilitate the isolation of the final product.

It is very frequently found that the conversion of the compound of the formula (VI) is not complete and that this amine remains frequently dissolved, whereas the major portion of the hydrochloride of the compound of the formula (I) precipitates as crystals. The yet unconverted portion of the compound of the formula (VI) is then very readily converted in a second operation, as follows:

The filtrate from the cyclisation step (see (b)) is neutralized with an aqueous base solution to release the compounds of the formulae (VI) and (I) which are extracted together with a water-immiscible solvent. This solution, which contains the compounds of the formulae (VI) and (I), is stirred with aqueous formaldehyde in a manner analogous to that described under (a) to convert the compound of the formula (VI) into one or more product(s) identical with those obtained under (a). The organic phase which contains those products, together with the compound of the formula (I) which undergoes no degradation, is then dried. The dried solution may be concentrated or used as such to undergo the cyclisation reaction effected under the conditions described under (b). Thus, the hydrochloride of the compound of the formula (VI) is found to precipitate in the form of crystals. The mother-liquors still contain some hydrochloride of the compound of the formula (I) and a very small amount of the hydrochloride of the compound of the formula (VI). When considered necessary, this filtrate may be recycled once more.

In cyclisation step (b), the reagents may also be added in the reverse order, i.e., the solution of hydrochloric acid in the polar solvent may be added to the mixed amines (of type IX, X, XI). It is then noted, however, that the yields are generally less satisfactory and vary as a function of the conditions used.

The following non limiting examples are given to illustrate the invention.

EXAMPLE 1

Preparation of 5-(2-chloro-benzyl)-4,5,6,7-tetrahydrothieno[3,2-c]pyridine (as the hydrochloride)

1. Preparation of 2-(2-thienyl)-ethanol (derivative (IIa); $R_2 = R_3 = H$)

Butyl lithium (100 moles; 6.40 kg) dissolved in hexane (64 liters) is added to thiophene (110 moles; 8.75 liters) mixed with dry tetrahydrofuran (10 liters), under an inert nitrogen atmosphere. The exothermic reaction is effected under refluxing conditions; addition of butyl lithium is effected over 1.5 hours, using suitable cooling means; the reaction medium is then cooled to about 10° C. and a solution of ethylene oxide (105 moles; 4.62 kg) in tetrahydrofuran (10 liters) is added thereto. The reaction is exothermic and the temperature is maintained below 25° C. by cooling. This step takes about 1 hour. The lithium thienyl alkoxide precipitates out.

6N hydrochloric acid is then added to neutralise the reaction medium. The organic layer is then separated, concentrated, and the residue is distilled under reduced pressure, to give 12.47 kg (Yield: 79%) 2-(2-thienyl)-ethanol.

2. Preparation of 2-(2-thienyl)-ethyl paratoluene sulfonate 8.32 kg (65 moles) of the 2-(2-thienyl)-ethanol obtained in 1. above are mixed with 12.68 kg (66.6 moles) paratoluene sulfonyl chloride and 6.8 kg (67.2 moles) triethylamine and with 63 liters diisopropyl ether at room temperature. After stirring during 70 hours, the reaction mixture is poured over 40 liters water. The organic phase is washed with carbonated water and then with pure water until neutral, after which it is dried over sodium sulfate. Evaporation of the solvent gives 16.62 g (Yield: 90.60%) 2-(2-thienyl)-ethyl paratoluene sulfonate.

3. Preparation of N-(2-chloro-benzyl)-2-(2-thienyl)-ethylamine hydrochloride 850 g (3 moles) 2-(2-thienyl)-ethyl paratoluene sulfonate and 850 g (6 moles) ortho-chlorobenzylamine are dissolved in 5.2 liters acetonitrile and the mixture is refluxed during 6.5 hours. After filtration, 630 g ortho-chlorobenzylamine paratoluene sulfonate are removed by filtration. The filtrate is concentrated and the residue is taken up into diisopropyl ether and 500 ml 2N sodium hydroxide. The organic phase is separated and is made acidic with 3N hydrochloric acid. The resulting hydrochloride precipitates out; it is collected by filtration, suction filtered and washed with acetone, to give 684 g (Yield: 78%) N-(2-chloro-benzyl)-2-(2-thienyl)-ethylamine hydrochloride.

This compound may also be obtained directly, via derivative (IIb), as follows:

To a solution of 87.5 ml thiophene (1.1 mole) in 100 ml tetrahydrofuran is added a solution of 64 g butyl lithium (1 mole) in 1 liter hexane, at a temperature of 35°–39° C. The mixture is cooled to 10° C. and a solution of 48 ml ethylene oxide (1.08 mole) in 50 ml tetrahydrofuran is added thereto in such a manner that the temperature does not exceed 25° C.

The reaction medium is then cooled to −20° C. and a solution of 190.50 g (1 mole) paratoluene sulfonyl chloride in 250 ml tetrahydrofuran is added thereto, while maintaining the temperature at about −20° C. The temperature of the mixture is then raised to 0° C. and ortho-chlorobenzylamine (282 g; 2 moles) is added thereto.

The resulting mixture is then refluxed during 18 hours, after which it is cooled and water (600 ml) is added thereto. The aqueous phase is extracted with diisopropyl ether and the combined organic phases are concentrated. The oily residue is taken up into diisopropyl ether and 520 ml 4N hydrochloric acid. The N-(2-chlorobenzyl)-2-(2-thienyl)-ethylamine hydrochloride precipitates out; it is then suction filtered and washed with acetone, to give 112 g of product (overall yield calculated on the basis of the butyl lithium: 39%).

4. Preparation of 5-(2-chloro-benzyl)-4,5,6,7-tetrahydrothieno[3,2-c]pyridine 15 g (0.052 mole) of the compound obtained in (3), 100 ml water and 5 ml of a 35% aqueous formaldehyde solution (0.58 mole) are heated at 90° C. during 15 minutes, after which 2N hydrochloric acid (100 ml) is added thereto and the resulting mixture is heated at 90° C. during 1.5 hour. After cooling, a slight precipitate is removed by filtration. The aqueous phase is made alkaline with 2N NaOH and is then extracted with 350 ml diisopropyl ether. The organic phase is washed with water, dried over sodium sulfate and concentrated, to give 11.32 g of a light orange oil.

This oil is then dissolved in isopropyl ether and, after addition of dry HCl, gives 10 g of a hydrochloride precipitate which is purified by recrystallization from boiling absolute ethanol (Yield: 64%).

EXAMPLE 2

Preparation of 5-(2-chloro-benzyl)-6-methyl-4,5,6,7-tetrahydro-thieno[3,2-c]pyridine (as the hydrochloride)

1. Preparation of 1-(2-thienyl)-2-propanoltosylate

To a cooled solution (0° C.) of 135 g (0.71 mole) tosyl chloride in 360 ml dry pyridine is added dropwise a solution of 98.1 g (0.69 mole) 1-(2-thienyl)-2-propanol in 300 ml dry pyridine.

The mixture is kept in the refrigerator during 65 hours and is then poured over 2.5 liters cold water. The resulting precipitate is filtered off, rinsed with water and dried (Yield: 182.8 g; 89%; M.p. = 68° C.)

2. Preparation of N-o.chlorobenzyl-1-methyl-2-(2-thienyl)ethylamine

A mixture of 18.2 g (0.0615 mole) of the tosylate obtained in (1), 17.4 g (0.123 mole) orthochlorobenzylamine and 50 ml toluene is refluxed during 24 hours. After cooling, water (50 ml) and 2N sodium hydroxide (35 ml) are added thereto and the resulting material is extracted with ether. The ether phase is treated with an aqueous 6N hydrochloric acid solution, with vigorous stirring. The precipitate which separates out is filtered, washed with ether and dried to give 11.6 g of material, m.p. = 166° C. (Yield: 66%).

3. Preparation of 5-o.chlorobenzyl-6-methyl-4,5,6,7-tetrahydro-thieno[3,2-c]pyridine (as the hydrochloride)

A mixture of 1 g of the amine hydrochloride obtained in (2), 20 ml water, 3 ml formalin (35% aqueous solution) and 0.5 ml concentrated hydrochloric acid is refluxed during 2.5 hours. After cooling, the mixture is made alkaline with a 2N sodium hydroxide solution and is then extracted with ether. The ether phase is dried and evaporated to dryness. The residue is purified by column chromatography on silica (eluent: benzene-ethyl acetate 7:3).

The resulting 5-o.chlorobenzyl-6-methyl-4,5,6,7-tetrahydro-thieno[3,3-c]pyridine is dissolved in ether and treated with one equivalent hydrochloric acid dissolved in ether. The resulting hydrochloride is recrystallized from a diisopropyl ether-isopropyl alcohol mixture (Yield: 300 mg; 28%; m.p. = 178°–182° C.).

EXAMPLE 3

Preparation of 5-(2-chloro-benzyl)-4,5,6,7-tetrahydro-thieno[3,2-c]pyridine via a two-step cyclisation (a) To N-(2-chloro-benzyl)-2-(2-thienyl)ethylamine (2515 g; 10 moles) is added, with stirring, a 35% formaldehyde aqueous solution (946 g; 11 moles). The reaction is immediate and slightly exothermic. The aqueous phase is decanted, washed with water and the organic phase is dried azeotropically, to give 2780 g intermediate products of step (a).

(b) The resulting mixture of intermediate products is poured over 5 liters of 5N HCl solution in dimethylformamide. The reaction is exothermic and the temperature rises to 45°–50° C., at which level it is maintained by external cooling. The addition is complete in about 30 minutes. Ten minutes after completion of the addition, the 5-(2-chloro-benzyl)-4,5,6,7-tetrahydro-thieno[3,2-c]pyridine hydrochloride begins to precipitate out. The reaction mixture is cooled to room temperature and is filtered on completion of the precipitation. The precipitate (1920 g) is washed with acetone. The filtrate still contains 330 g of the desired product and 325 g N-(2-chloro-benzyl)-2-(2-thienyl)ethylamine. Thus, the conversion rate of this amine is 87.1% and the yield of 5-(2-chloro-benzyl)-4,5,6,7-tetrahydro-thieno[3,2-c]pyridine is 86%, the major portion of which is obtained as a precipitate.

In order to recover the unreacted starting amine and the unprecipitated portion of the desired product, the filtrate is treated in the following manner:

The filtrate is poured over water containing sodium hydroxide; the amines thus released are extracted with methylene chloride which may be removed, or not, for another formalin treatment and another cyclisation according to a procedure similar to that described above. The conversion rates and the yields based on the N-(2-chloro-benzyl)-2-(2-thienyl)-ethylamine contained in the filtrate of the primary operation are approximately the same.

The derivatives set forth in following Tables I and II were prepared according to the above-described procedures.

TABLE I

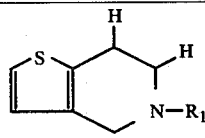

| Compound No. | $R_1$ | M.p. or b.p. (° C) | Yield (%) |
|---|---|---|---|
| 1 | $CH_3$ | b.p. 52–54° /0.1 mm Hg | 39 |
| 2 | $(CH_2)_6CH_3$ | b.p. 118° /0.5 mm Hg | 42 |

TABLE I-continued
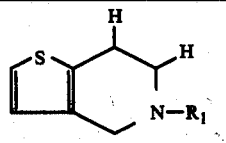
| Compound No. | R₁ | M.p. or b.p. (° C) | Yield (%) |
|---|---|---|---|
| 3 | —CH₂—C₆H₅ | 240° (hydrochloride) | 40 |
| 4 | —CH₂—(2-CH₃)C₆H₄ | 208–210° (hydrochloride) | 46 |
| 5 | —CH₂—(3-CH₃)C₆H₄ | 215° (hydrochloride) | 47 |
| 6 | —CH₂—(4-CH₃)C₆H₄ | 260° (hydrochloride) | 38 |
| 7 | —CH₂—(2-F)C₆H₄ | 168° (maleate) | 48 |
| 8 | —CH₂—(2-F)C₆H₄ | 216° (methiodide) | 51 |
| 9 | —CH₂—(4-F)C₆H₄ | 215° (hydrochloride) | 50 |
| 10 | —CH₂—(2-Cl)C₆H₄ | 190° (hydrochloride) | 38 |
| 11 | —CH₂—(2-Cl)C₆H₄ | 212° (maleate) | 44 |
| 12 | —CH₂—(2-Cl)C₆H₄ | 182° (methiodide) | 48 |

TABLE I-continued
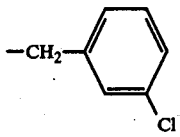
| Compound No. | R₁ | M.p. or b.p. (° C) | Yield (%) |
|---|---|---|---|
| 13 | —CH₂—C₆H₄—Cl (3-Cl) | 200° (hydrochloride) | 46 |
| 14 | —CH₂—C₆H₄—Cl (4-Cl) | 240° (hydrochloride) | 52 |
| 15 | —CH₂—C₆H₃(Cl)₂ (2,3-diCl) | 200° (hydrochloride) | 49 |
| 16 | —CH₂—C₆H₃(Cl)₂ (3,4-diCl) | 210° (hydrochloride) | 32 |
| 17 | —CH₂—C₆H₄—OH (3-OH) | 122° | 38 |
| 18 | —CH₂—C₆H₄—OH (4-OH) | 240° (hydrochloride) | 49 |
| 19 | —CH₂—C₆H₄—O—COCH₃ | 86° | 43 |
| 20 | —CH₂—C₆H₄—OCH₃ (2-OCH₃) | 90° | 34 |
| 21 | —CH₂—C₆H₄—OCH₃ (3-OCH₃) | 200° (hydrochloride) | 46 |
| 22 | —CH₂—C₆H₄—OCH₃ (4-OCH₃) | 215° (hydrochloride) | 52 |

TABLE I-continued
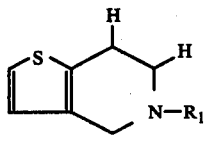
| Compound No. | $R_1$ | M.p. or b.p. (° C) | Yield (%) |
|---|---|---|---|
| 23 | 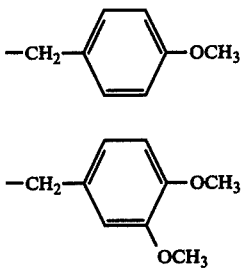 | 100° (methiodide) | 48 |
| 24 | 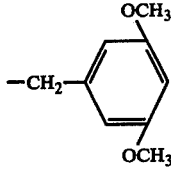 | 210° (hydrochloride) | 35 |
| 25 | 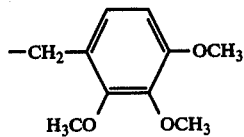 | 195° (hydrochloride) | 41 |
| 26 | 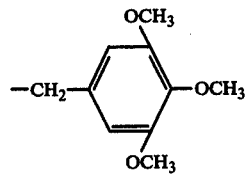 | 196–198° (hydrochloride) | 43 |
| 27 | 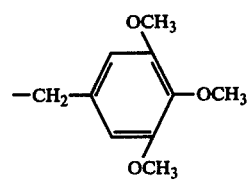 | 205° (hydrochloride) | 32 |
| 28 | 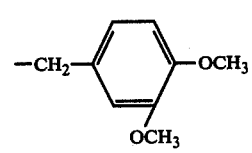 | 195° (methiodide) | 46 |
| 29 | 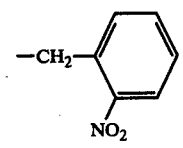 | 230–235° (hydrochloride) | 38 |
| 30 | 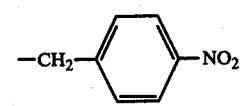 | 180° (hydrochloride) | 48 |
| 31 |  | 119–121° | 46 |

TABLE I-continued

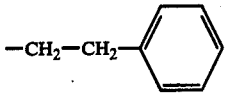

| Compound No. | $R_1$ | M.p. or b.p. (° C) | Yield (%) |
|---|---|---|---|
| 32 | —CH$_2$—CH$_2$—C$_6$H$_5$ | 226° (hydrochloride) | 38 |
| 33 | —CH$_2$—CH=CH—(2-Cl-C$_6$H$_4$) | 176° (hydrochloride) | 29 |
| 34 | —CH$_2$—(1-naphthyl) | 120° | 48 |
| 35 | —CH$_2$—(5-chloro-2-thienyl) | 200° (hydrochloride) | 37 |
| 36 | —CH$_2$—CH(OH)—C$_6$H$_5$ | 164–166° (hydrochloride) | 42 |
| 37 | —CH(CH$_3$)—CH(OH)—C$_6$H$_5$ | 230° (hydrochloride) | 51 |
| 38 | —CH$_2$—CH(OH)—(4-biphenylyl) | 210° (hydrochloride) | 55 |
| 39 | —CH$_2$—CH(OH)—(4-F-C$_6$H$_4$) | 124° | 47 |
| 40 | —CH$_2$CH(OH)—(4-Cl-C$_6$H$_4$) | 195° (hydrochloride) | 41 |
| 41 | —CH$_2$CH(OH)—(4-OH-C$_6$H$_4$) | 216–218° (hydrochloride) | 44 |
| 42 | —CH$_2$CH(OH)—(2-OCH$_3$-C$_6$H$_4$) | 224° (hydrochloride) | 37 |

TABLE I-continued

![structure]

| Compound No. | R₁ | M.p. or b.p. (° C) | Yield (%) |
|---|---|---|---|
| 43 | —CH₂—CH(OH)—C₆H₄(OCH₃) (meta) | 170° (hydrochloride) | 38 |
| 44 | —CH₂—CH(OH)—C₆H₄—OCH₃ (para) | 206–208° (hydrochloride) | 42 |
| 45 | —CH₂—CH(OH)—C₆H₃(OCH₃)(H₃CO) | 106° | 41 |
| 46 | —CH₂—CH(OH)-thienyl | 150° (fumarate) | 48 |
| 47 | —CH₂—C₆H₄—F | 190–194° (hydrochloride) | 39 |
| 48 | —CH₂—C₆H₄—Cl | 179–180° (hydrochloride) | 32 |
| 49 | —CH₂—C₆H₄—NO₂ | 178–180° (hydrochloride) | 44 |

Having now described my invention what I claim as new and desire to secure by Letters Patent is:

1. Process for the preparation of thieno-pyridine derivatives having the formula:

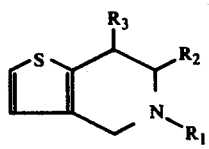    (I)

in which R₁ is a member selected from the group consisting of C₁₋₇ alkyl; phenyl lower alkylene; phenyl lower alkylene in which the phenyl is substituted with 1 to 3 substituents selected from the group consisting of lower alkyl, hydroxy, lower acyloxy, lower alkoxy, nitro and halogen; naphthyl lower alkylene; thienyl lower alkylene; diphenyl lower alkylene; phenyl hydroxy-lower-alkylene; phenyl hydroxy-lower-alkylene in which the phenyl is substituted with 1 to 3 substituents selected from the group consisting of lower alkyl, hydroxy, lower acyloxy, lower alkoxy, nitro and halogen; naphthyl hydroxy-lower-alkylene; thienyl hydroxy-lower-alkylene; and diphenyl hydroxy-lower-alkylene; R₂ is selected from the group consisting of hydrogen and lower alkyl; and R₃ is hydrogen, comprising:

(a) reacting a derivative having the formula:

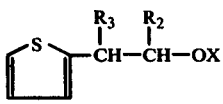    (II)

in which R₂ and R₃ are as defined for formula (I) and X is selected from the group consisting of hydrogen, an alkali metal and a radical MgY in which Y represents halogen, with a halosulfonyl derivative having the formula:

$$Hal - SO_2 - R_4 \qquad (III)$$

in which Hal represents halogen and $R_4$ is selected from the group consisting of methane sulfonyl, trichloromethane sulfonyl, trifluoromethane sulfonyl, benzene sulfonyl, paratoluene sulfonyl, m. acetyl benzene sulfonyl and p. bromophenyl sulfonyl, to give a compound having the formula:

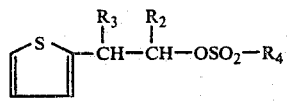

(b) reacting said derivative (IV) with an amine of the formula

$$R_1 - NH_2 \qquad (V)$$

in which $R_1$ is as defined for formula (I), to give a compound having the formula:

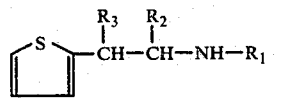

and (c) subsequently cyclising said derivative (VI) with formaldehyde to give the derivative of the formula (I).

2. Process as claimed in claim 1, wherein the reaction of step (a) is effected in the presence of a base selected from the group consisting of the organic and inorganic bases when a derivative of the formula (II) in which X is hydrogen is used.

3. Process as claimed in claim 1, wherein a derivative of the formula (II) in which X represents a lithium atom is used in step (a).

4. Process as claimed in claim 1, wherein step (b) is effected with an excess of the amine.

5. Process as claimed in claim 1, wherein the cyclisation of step (c) is effected in a single stage in acidic medium, within an inert solvent.

6. Process as claimed in claim 1, wherein the cyclisation is effected in two successive stages comprising (a) reacting formaldehyde with the compound of the formula (VI) in aqueous medium and isolating the water-free product, and subsequently (b) reacting the compounds obtained in (a) with a solution of dry hydrochloric acid in an aprotic polar solvent.

7. Process as claimed in claim 6, wherein the aprotic polar solvent is dimethylformamide.

8. Process as claimed in claim 6, wherein the aprotic polar solvent is selected from the group consisting of dimethyl sulfoxide, N-methyl pyrrolidone and N,N-dimethylacetamide.